United States Patent [19]
Fjelstad

[11] Patent Number: 5,810,586
[45] Date of Patent: Sep. 22, 1998

[54] METHOD AND APPARATUS FOR DETERMINING PLACEMENT OF PATTERNS FOR DENTURES

[76] Inventor: Harold K. Fjelstad, 6616 Fourth Ave. South, Minneapolis, Minn. 55423-2420

[21] Appl. No.: 627,886

[22] Filed: Apr. 3, 1996

[51] Int. Cl.[6] .................................................. A61C 19/04
[52] U.S. Cl. ................................................. 433/68; 33/513
[58] Field of Search ............................... 433/69, 71, 68, 433/213, 214; 33/513, 514

[56] References Cited

U.S. PATENT DOCUMENTS

| | | | |
|---|---|---|---|
| 1,944,601 | 1/1934 | Gulick | 433/68 |
| 2,107,534 | 2/1938 | Houser | 33/513 |
| 2,154,148 | 4/1939 | Butts | 33/513 |
| 2,566,903 | 9/1951 | Moran | 433/68 |
| 2,841,871 | 7/1958 | Miller | 433/68 |
| 4,096,637 | 6/1978 | Stade . | |
| 4,126,938 | 11/1978 | Lee | 433/69 |
| 4,695,252 | 9/1987 | Edwardson | 433/73 |
| 4,836,779 | 6/1989 | Beu | 433/73 |
| 4,843,720 | 7/1989 | Kim | 33/513 |
| 5,090,901 | 2/1992 | Levandoski | 433/56 |

*Primary Examiner*—Cary E. O'Connor
*Attorney, Agent, or Firm*—Patterson & Keough, P.A.

[57] ABSTRACT

This invention consists of a method and apparatus for making patterns which establish the specific vertical dimensions and positions for patterns for the making of dentures which will provide a natural occlusion upon replacement of natural teeth.

6 Claims, 6 Drawing Sheets

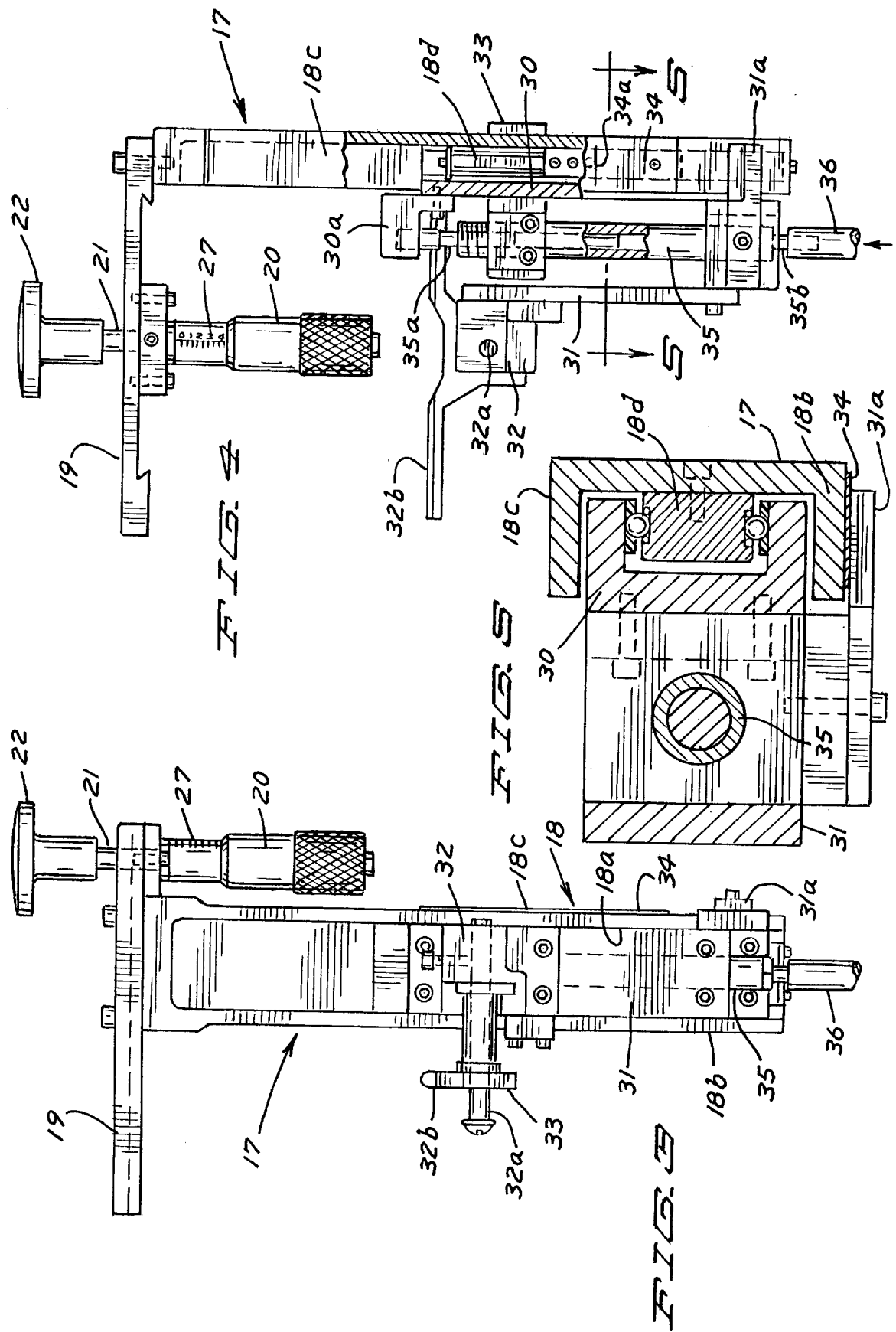

METHOD AND APPARATUS FOR DETERMINING PLACEMENT OF PATTERNS FOR DENTURES

BACKGROUND OF THE INVENTION

1. Field of the Invention

Dental pattern making methods and devices determining the relative positions of patterns for dentures in the replacement of natural teeth.

2. Description of Prior Art

There has been a long and intensive development of various methods and devices to determine the placement of upper and lower dentures and their relative positions in the replacement of natural teeth to restore a natural occlusion. This is evidenced by the large number of patents issued for this purpose and these have been issued over a long period of time.

The endeavor in this field has been to establish specific reference points relative to the positions of the teeth of the upper and lower jaws such that these reference points establish the exact positions of patterns for replacement by dentures whereby a natural bite or occlusions is provided.

Many of the devices described in prior art patents are too complex for practical operation and do not provide the degree of accuracy required for a suitable fitting of dentures. A major fault has been in the inability to provide stable reference points which can be accurately ascertained to determine the placement of dentures or of patterns for dentures after all natural teeth having been extracted.

Used to establish reference points have been ear openings with lip support as in U.S. Pat. Nos. 5,090,901 and 3,464,115, for example, and with these any particular position for the placement of dentures is difficult to reproduce particularly in vertically spacing or dimensioning the dentures.

Used also, has been a frame supported on ears and attached to a transverse rod supported upon the bridge of a patient's nose and a lower frame is attached to the lower jaw with a stylus being used over a recording plate to obtain measurements. Such a device is so complex that its use is discouraged.

These and further examples of the prior art are found in U.S. Pat. Nos. 5,090,901; 4,836,779; 4,695,252; 4,096,637; 4,126,938; and these are examples of a great many other patents showing a like state of the art.

The invention herein, as will be described, represents significant improvement and simplicity and assures the establishment of a natural bite in the dentures made.

SUMMARY OF THE INVENTION

A specific object of the invention herein is to establish specific reference points relative to natural teeth which reference points are precisely ascertained for the placement of dentures and survive the extraction of the natural teeth.

It is also an object herein to provide a method and apparatus for precisely making patterns of the upper teeth or maxilla and of the lower teeth or mandible in a closed mouth with natural teeth for the purpose of having dentures made.

It is a more significant object herein to provide a method and apparatus to position patterns for dentures in the same place in the mouth as occupied by the natural replaced teeth which will result in a bite of the dentures to which the patient has been accustomed and thus no breaking-in period is required by the patient to re-establish a natural occlusion.

Further, it is an object herein to simplify the procedure for the exact replacement of natural teeth by dentures.

These and other objects and advantages on the invention will be set forth in the following description in connection with the accompanying drawings in which like reference characters refer to similar parts throughout the several views.

BRIEF DESCRIPTION OF THE DRAWINGS

FIG. 3 is a side elevational view of the device herein;

FIG. 4 is a rear elevational view of the device herein;

FIG. 5 is a sectional view taken in line 5—5 of FIG. 4 as indicated;

DESCRIPTION OF A PREFERRED EMBODIMENT

Figure 1:
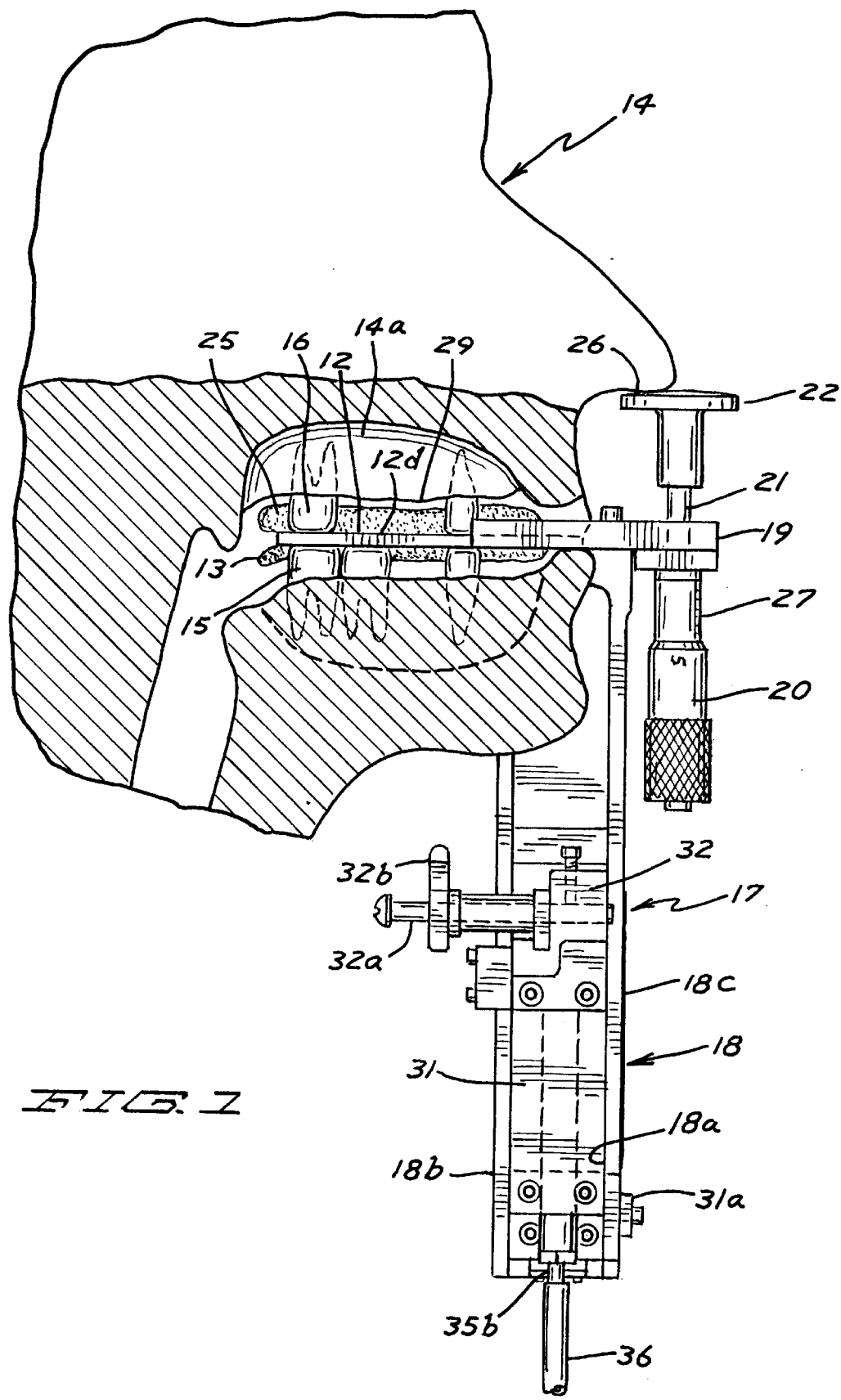
FIG. 1 is a side elevational view of a denture pattern registration device and bite plate, partially in dotted line, in one operating position.

The method herein together with its attendant apparatus or device is described to disclose the specific steps undertaken to make patterns and ascertain their precise positions in the mouth of a patient for upper and lower dentures for the placement of said patterns in an articulator for the making of the dentures, said positions being indicated by reference points which survive the extraction of the natural teeth of a patient. The essential element of teaching herein is the establishment of reference points.

The first step is in making a pattern for an upper denture and that is to take a bite plate 12, apply a layer of impressionable material 13 such as softened wax to the lower side 12a of said bite plate. Insert the bite plate into the mouth 14a of the patient 14 to carefully position the same over the lower teeth 15 therein and then have the upper teeth 16 therein bite firmly upon the bite plate to cause the lower teeth to bite through said wax layer to the bite plate to make a good impression. At least three teeth must penetrate to the bite plate to have said bite plate seat solidly on said lower teeth and have a direct relation to the vertical movement of the lower jaw which is referred to as TMJ (temporomandibular).

If a third tooth impression has not penetrated through the wax layer down to the bite plate, an impression, not here shown, will be selected and have its bottom cleared down to the bite plate and refilled with a quick-setting material, such as Denta Stone, to a height for a tooth engagement. The bite plate is re-inserted into the patient's mouth in the same location as originally for a third tooth impression whereby the bite plate, upon removal from the mouth, has a good impression of the lower teeth.

Preparing a bite plate to make a pattern is a procedure known in the art. The novelty herein, as will be described, is present in establishing reference points for the positioning of patterns in a closed mouth to provide the same occlusion which was present with the replaced natural teeth.

Next, a reference point will be established of the position of the bite plate in a closed mouth when it comes up against the upper teeth. For this purpose a registration device 17 of the invention herein is used.

Said registration device has a dual function to determine and fix with regard to the mouth of a patient a reference point or a position for the location in a closed mouth of a pattern for an upper denture and also for a reference point or a position for the location of a pattern for a lower denture.

The objective here is the creation of a pattern for an upper and a lower denture which precisely represent in the vacated space of a mouth the same positions as the natural teeth prior to their extraction. Thus, the pattern, when mounted in an articulator, are in the same relative positions as were the natural teeth prior to their extraction and the dentures made have the same occlusion as was had by the replaced natural teeth.

With reference to FIGS. 1, 3, 6, 8 and 9 said registration device for determining the position of an upper denture pattern comprises a vertically disposed U-shaped channel member 18 having mounted thereon at right angles thereto a bite plate holding member 19 having a pair of opposed slots 19a and 19b which receive therein said bite plate 12.

Said holding member 19 has mounted thereon, a micrometer 20 having an upwardly extending spindle 21 having at its top a disc wheel 22 which is elevated by rotation of said micrometer.

Referring to FIG. 1, said registration device has mounted therein said bite plate 12 with the impression of the lower teeth in the wax layer 13 at its under side. Said bite plate thus held is given at its upper side 12d a coat of mold forming impressionable material 25 such as Alginate or an equivalent to a thickness of a tooth height and with this coating said bite plate is carefully inserted into the mouth of the patient to be positioned upon said lower teeth and moved upwardly by a closing of the mouth to become engaged by said upper teeth and the bite plate is held carefully in this position until the impressionable material 25 sets up (approximately two minutes). In the meantime, the micrometer is rotated to raise its disc wheel 22 to engage without pressure the base 26 of the patient's nose. A micrometer reading 27 is recorded and will be used to establish the vertical dimension in the pattern after the extraction and healing of the gum. At this time we have established the centric and laterally the position of the upper teeth relative to that of the lower teeth through the bite plate. The bite plate is removed from the patient's mouth and at this time the upper teeth may be extracted. It is noted that the position of the device 17 is determined by the placement of the bite plate in the mouth of the patient.

Said bite plate now has formed at its upper side an open-faced mold 23 which has in it the arrangement and location of the upper teeth relative to the upper healed gum.

A cast-forming material such as Denta Stone is poured into said mold to a depth of about the height of a tooth allowing it to overflow onto the bite plate and around an anchor nut 12b shown on the bite plate and into the recess location holes 12c to be detachably attached to said bite plate. This practice is known in the art and is not shown. After the cast-forming material has set, the cast 24 formed by it may be removed to remove all impressionable material from the bite plate, the cast then will be re-attached to the bite plate as in FIG. 9. With the patient's upper gum 29 healed, the following steps are taken.

The bite plate is again inserted into the bite plate holding 19 and the cast 24 upon the bite plate becomes like a tray holding impressionable material 13, such as softened wax, to a depth or thickness of a tooth height, which is on the order of 7–8 mm, following which said bite plate is again carefully inserted into the mouth of the patient to be accurately positioned with the previous underside wax impression upon the lower teeth.

Said upper healed gum will close down upon said bite plate and into said cast and said impressionable material coated thereon. Said gum will close down into said impressionable material to the extent of said first reference point measurement of said disc wheel engaging the base 26 of the patient's nose. The pressure of the gum upon the impressionable material overlying the cast will squeeze out excess of the impressionable material and will then have positioned the cast 24 with the impressionable material thereon into the same location and vertical dimension within the mouth as when the reference point was first established. Thus, there is provided a pattern for an upper denture which has in it the precise location of each natural tooth and the vertical dimension and location thereof made relative to the healed gum such as the natural teeth were in the mouth prior to extraction.

Figure 2:
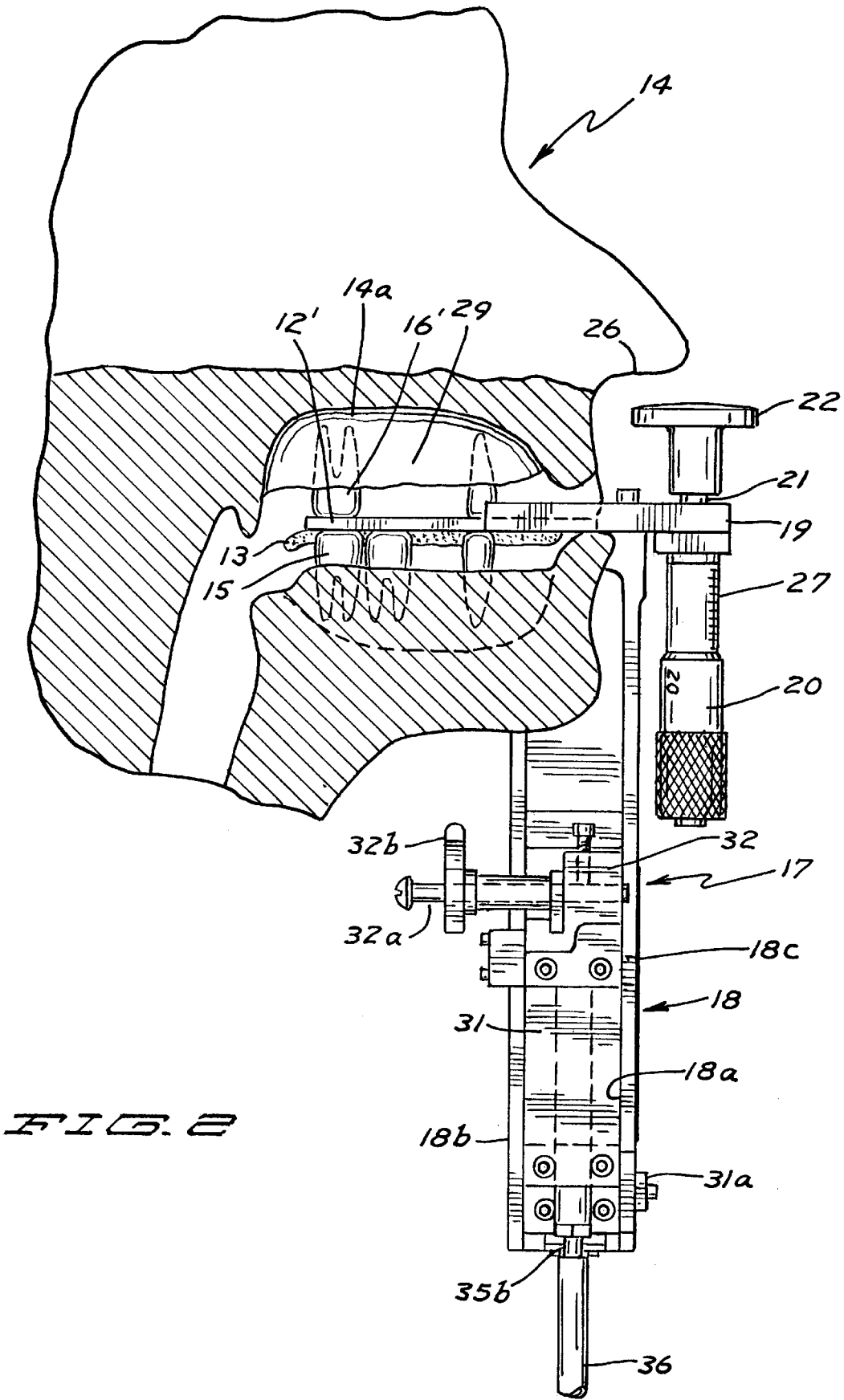
FIG. 2 is a view similar to that of FIG. 1 of an alternate operating position.
Figure 6:
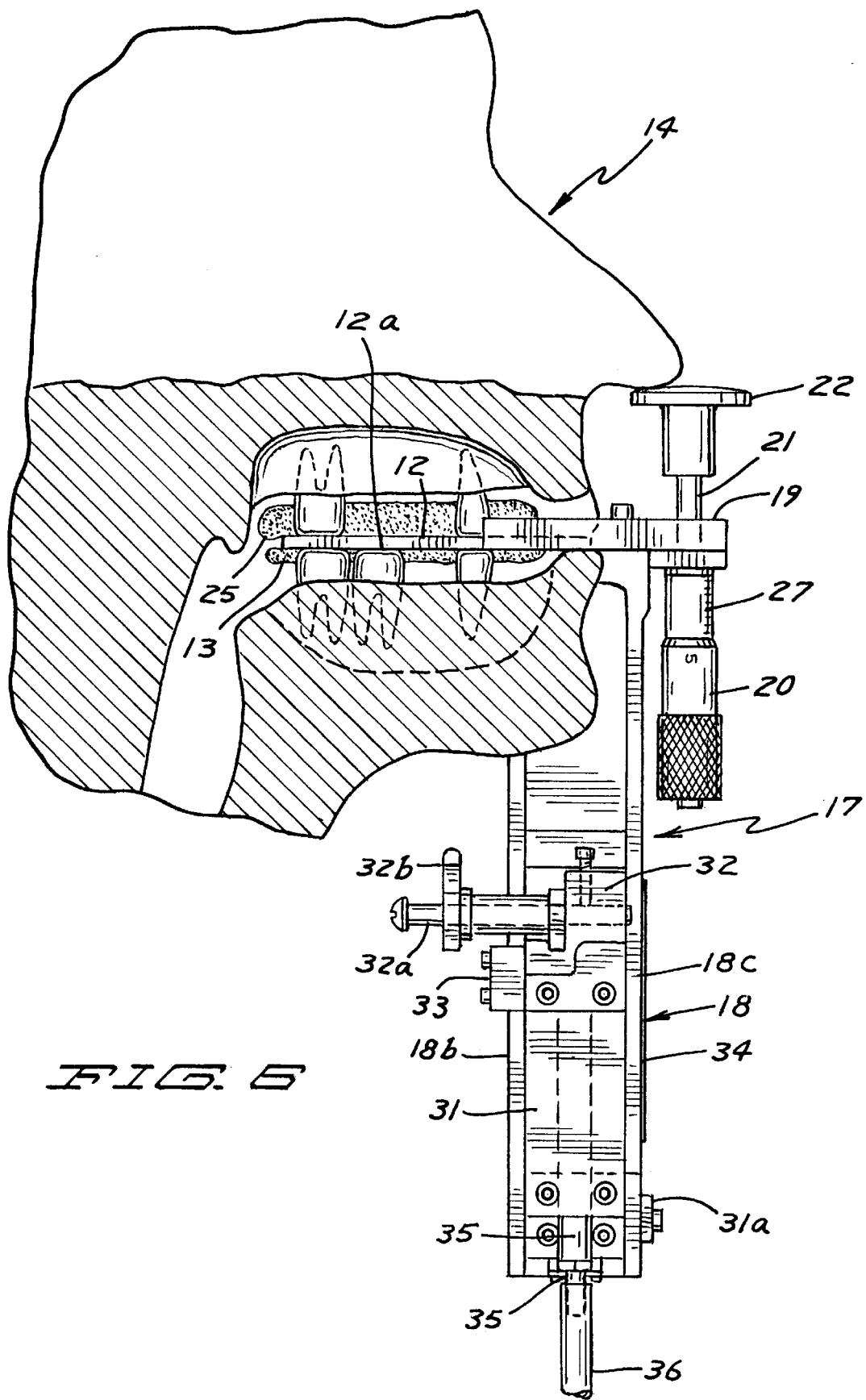
FIG. 6 is a view similar to that of FIG. 1 of a related operating position.

Reference is now had to FIGS. 3–5 and described will be the function of said registration device with regard to making a lower denture pattern and more particularly relating to the positioning of the pattern with reference to FIGS. 2 and 3.

Referring first to said registration device, as indicated, it comprises channel member 18 having a channel 18a therein having side walls 18b and 18c and having therein a rail 18d upon which is a ball slide 30 having mounted thereon an elongated vertical angled bracket 31, said bracket having an arm 31a sliding along the side wall 18c on which is carried a removable marking strip or sticker 34 to be further described.

Mounted on said bracket 31 is a bracket 32 having a rotatable shaft 32a projecting outwardly thereof on which is carried a shoulder bracket 32b as shown in FIG. 4.

Carried by said side wall 18b and being angled upwardly thereof to extend over said ball slide is a bracket 33. Carried by said bracket 33 and overlying and extending longitudinally of said ball slide is an air cylinder 35 having therein a rod 35a to be projected by air pressure from tube 36 running from a controlled air supply, not shown, to the inlet 35b of said cylinder.

An end wall 30a at the upper end of said ball slide is moved by a projection of said rod 35a as will be further described.

Prior to the use of said registration device as relating to a pattern for a lower denture and in keeping with the description of a pattern for an upper denture, a bite plate, hereafter 12', is coated on its upper surface 12'a with a layer of softened impressionable material 13 such as wax, to a depth on the order of 3–4 mm and the same is carefully positioned in the patient's mouth to have the patient bite down thereon through the coating of said material down to the surface of said bite plate to establish an impression of the upper teeth which at this point have been replaced by a new upper denture 16'. This is the same procedure as was carried out with the bite plate 12 on its reverse side with the upper denture.

Said bite plate is then removed from the patient's mouth and mounted onto said bite plate holding member 19. Said bite plate, thus attached, is re-inserted into the patient's mouth to be held against said upper denture therein. While thus held, said cylinder 35 is charged with pressurized air causing the rod 35a to extend or project moving upwardly said shoulder bracket 32b to engage and follow the upward closing of the lower jaw 15a. The air pressure actuating said cylinder will be continued to rise to a predetermined pressure level such as of 15 psi for a good contact. With the lower jaw fully closed, a line 34a is scribed onto said sticker strip 34 to indicate the position of said sliding arm 31a. The shoulder bracket 32b will have engagement with the lower jaw underlying the same. Thus, a reference point is established as to a vertical position of the lower jaw when the lower teeth has engaged the bite plate relative to the position of the upper denture in a closed mouth, this being the distance between the bite plate and the bottom surface of the lower jaw.

The bite plate is removed from the patient's mouth and from said holding member. As described in connection with said upper teeth, the bottom surface of said bite plate is then coated with said impressionable mold-forming material, such as Alginate, to a depth of 7–8 mm (the height of a tooth). The bite plate is mounted onto said bite plate holding member 19 and is quickly returned to the patient's mouth being carefully located to be in the same place as previously with regard to the upper denture. The patient next raises his lower teeth to make a good impression thereof in the impressionable material on the underlying surface of said bite plate. Said bite plate 12' is removed from said patient's mouth and from said bite plate holding member having at its underlying side an open face mold, not unlike the mold 23, of the arrangement and location of the lower teeth, the mold not here being shown. At this point, the lower teeth are extracted.

Next, a cast-forming material such as of Denta Stone, is poured into said open-faced mold, as in the case of the mold 23, to a depth of the length of a tooth and said material is caused to flow over said mold onto the bottom side or underlying surface of the supporting bite plate, onto said anchor nut 12b thereon and into the recess holes 12c therein to be detachably secured to said bite plate as in the case of the cast 24. After said cast-forming material has set, the cast is removed from the bite plate for the removal of all other material from said underlying surface thereof. The cast is then re-attached to the underlying surface of said bite plate.

Figure 7:
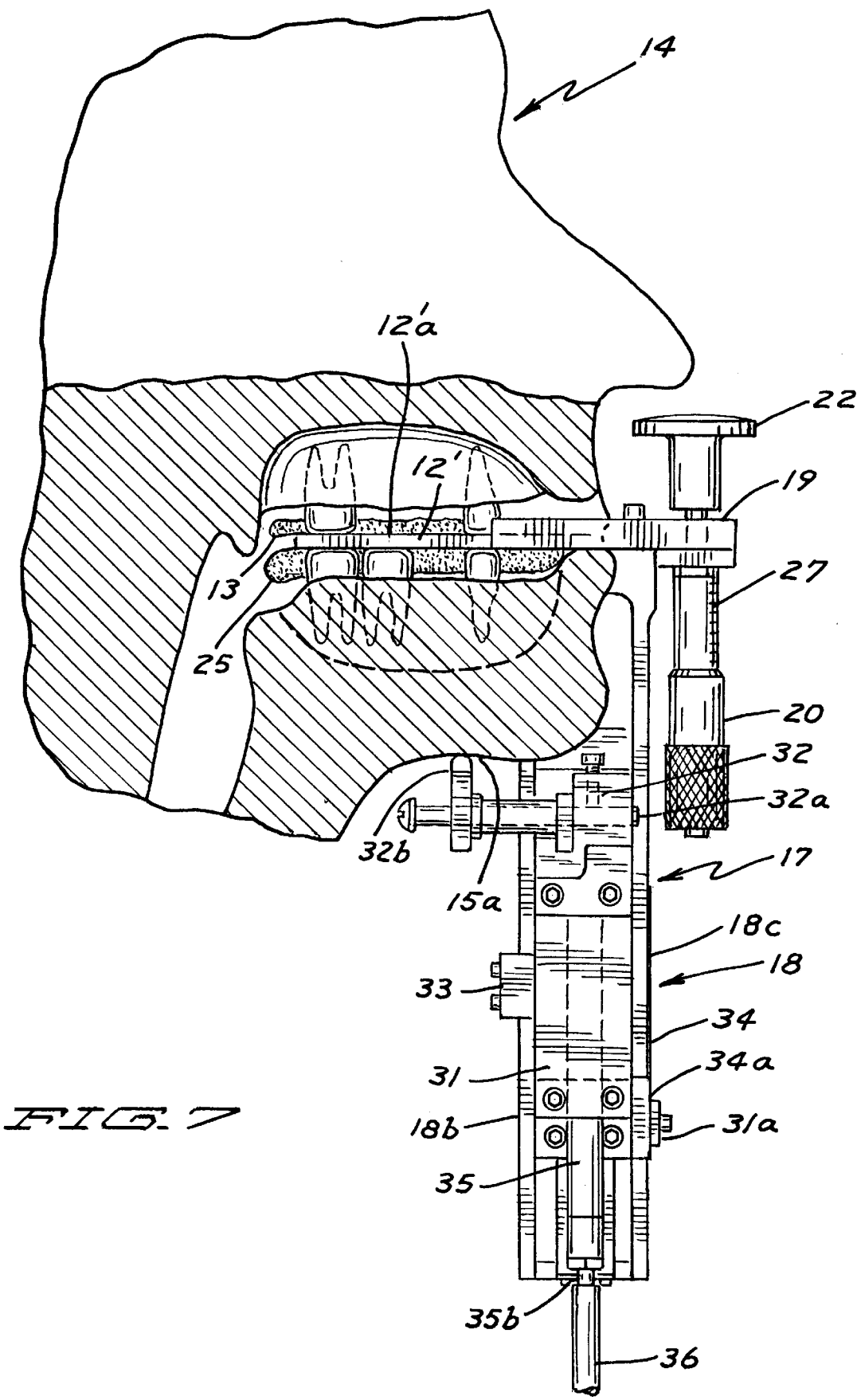
FIG. 7 is a view similar to that of FIG. 2 showing a related operating position.
Figure 8:
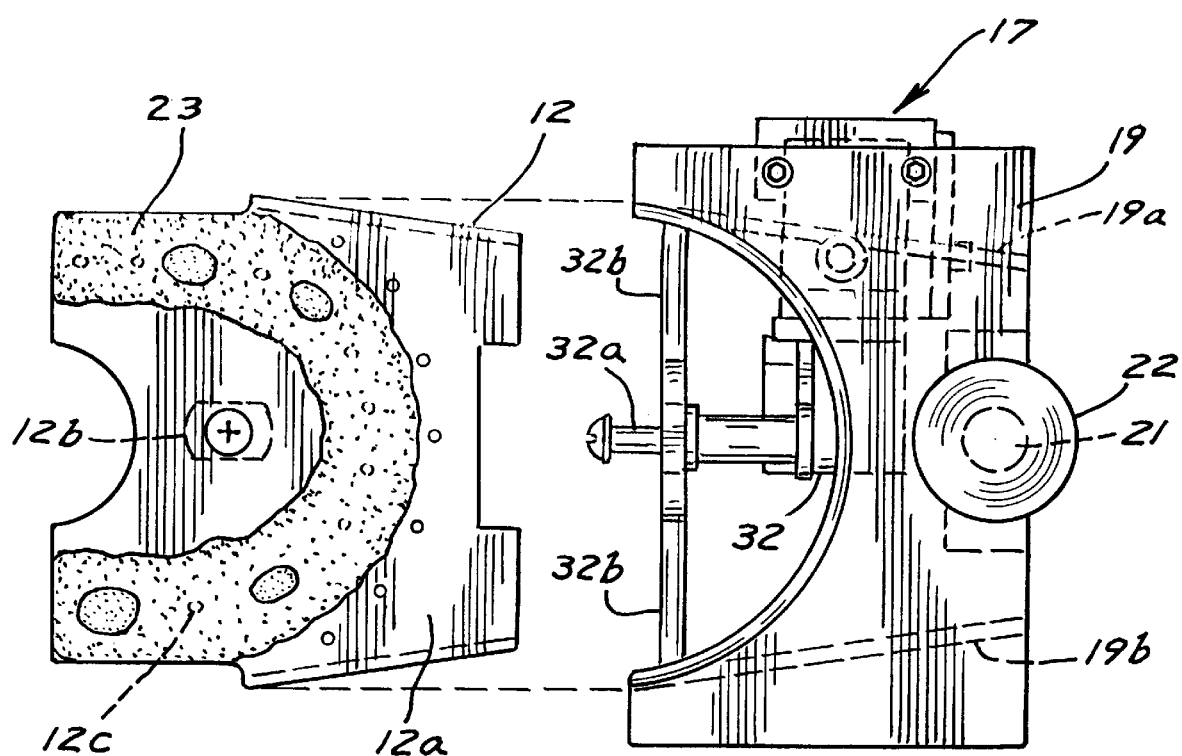
FIG. 8 is a top plain view of the device herein showing a portion thereof in dotted line and the extension of a member held thereby.
Figure 9:
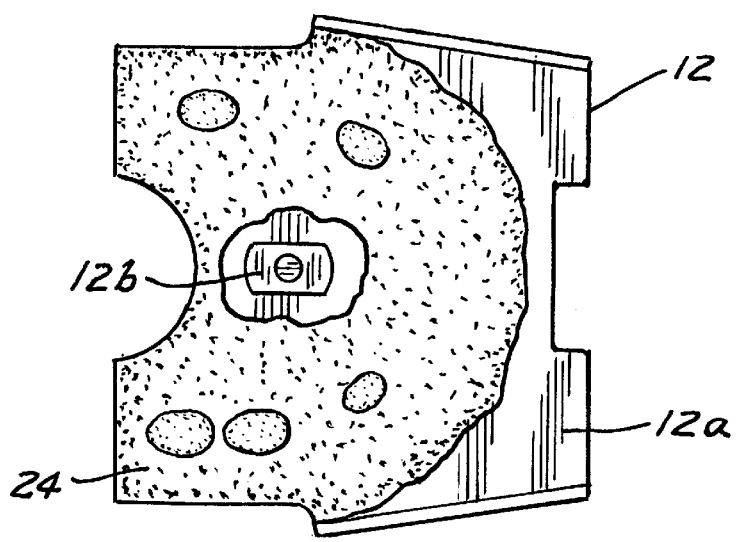
FIG. 9 is a top plain view of a member held by the device herein.

When the patient's lower gums have become sufficiently healed, the cast on said bite plate will have a coating of said impressionable material such as softened wax placed thereon, said bite plate will again be mounted onto said holding member 19 and re-inserted into the patient's mouth to be located precisely upon the upper denture and held firmly thereon (FIG. 7). At the same time, with the registration device 17 positioned as shown in FIG. 7, the air cylinder 35 is actuated by air pressure as of 15 psi which causes the shoulder bracket to engage the lower jaw and follow its upward movement as the lower gum is moved upwardly to engage and press against said impressionable material coating on said bite plate of said cast to the extent of said sliding arm reaching said previously made scribed line 34a at which point the patient has closed his lower jaw. Further, at this point, the excess impressionable material on the cast has been squeezed out whereby the cast and the impression made therein are in the same vertical and centric positions as were the nature teeth being replaced.

The air cylinder is shut off when the scribed line is reached and the registration device and bite plate mounted thereon are removed from the patient's mouth. The cast is removed from the bite plate having formed a pattern created for the lower denture. This pattern for the lower denture provides a true centric relation with the upper denture and provides a vertical dimension and vertical position which are the same as the of the natural teeth replaced.

As indicated herein, the upper denture is prepared prior to the lower denture in the making of the patterns herein. Although the procedure herein provides for a set of dentures, it is apparent that either an upper or a lower denture may be made with the method and apparatus as herein described. Further adjustment can readily be made for any shrinkage of gums which may occur.

Thus, it is seen that there have been provided definite measurements by means of the reference points indicated to establish the positions of patterns in their making as well as their vertical dimensions for the making of dentures therefrom in the replacement of natural teeth.

It will, of course be understood that various changes may be made in the form, details and arrangement of the method and apparatus herein without departing from the scope of the invention such as defined in the appended claims.

What is claimed is:

1. A method and apparatus to predetermine the vertical dimensions and positioning of patterns for a set of dentures in the mouth of a patient to provide the same occlusion as of the natural teeth replaced, consisting of adapting the bottom side of a first bite plate to have an impression thereon of the lower teeth in the mouth of a patient, positioning said bite plate against the upper teeth in a closed mouth, measuring the distance from said bite plate to the base of the nose of the patient for a first reference point, coating said bite plate to have an impression made thereon of said upper teeth to form an open-faced mold, extracting the upper teeth of said patient leaving the upper gum bare, forming a cast of said mold, coating said cast with an impressionable material, positioning said bite plate and cast upon said lower teeth closing said lower teeth upwardly upon said upper gum for an impression thereof to the extent of said first reference point providing a vertical dimension and position for said cast to be in the same position as were the extracted natural teeth whereby a pattern for an upper denture is formed, adapting a second bite plate to have an impression thereon of said upper denture as positioned in said patient's mouth, inserting said second bite plate to engage said upper denture, closing upwardly said lower teeth and the lower jaw of said patient measuring the distance from beneath said jaw to said second bite plate for a second reference point, adapting said second bite plate to receive an impression thereon of said lower teeth to form an open-faced mold, forming a cast of said mold and coating said cast with an impressionable material, inserting said second bite plate to engage said upper denture, closing upwardly said lower jaw and teeth for engagement with said impressionable material on said cast to the measured extent of said second reference point, for a vertical dimension of said cast and its position in a closed mouth, and removing said cast from said second bite plate, the cast becoming a pattern for a lower denture.

2. A method and apparatus to predetermine the vertical dimensions and positioning of patterns in the mouth of a patient for the making of dentures to be in the same relative position to provide the same occlusion as of the natural teeth replaced, consisting of coating the bottom side of a first bite plate and having an impression made thereon of the lower teeth in the closed mouth of a patient, mounting said bite plate in a registration device, inserting said bite plate into the mouth of the patient with said registration device holding the same against the upper teeth with said lower teeth engaged in the bottom impression thereof, measuring with said registration device the distance from said bite plate to the base of the patient's nose for a first reference point, removing said bite plate from said registration device, coating said bite plate on its upper side with an impressionable material having an impression made therein of said upper teeth under the applied pressure of said lower teeth to form an open-faced mold, extracting the upper teeth of said patient leaving the upper gum of said mouth bare, forming a cast of said mold, coating said cast with an impressionable material, mounting said bite plate and cast in said registration device, positioning said bite plate and cast upon said lower teeth closing the same upwardly upon said upper gum to the extent of said first reference point as indicated on said registration device squeezing out excess impressionable material to be in the same vertical position and have the same vertical dimension as the extracted teeth whereupon said cast is removed from said bite plate becoming a pattern for an upper denture to be made therefrom, coating a second bite plate with an impressionable material on its upper side, mounting said second bite plate in a said registration device, inserting said second bite plate against the upper dentures in the mouth of said patient, closing the lower teeth and lower jaw of said patient against said second bite plate, measuring with said registration device the distance from beneath said lower jaw to said second bite plate for a second reference point, coating the bottom side of said second bite plate with a molding material, inserting said second bite plate into patient's mouth against the upper denture therein closing the lower teeth thereagainst to form an open-face mold having the impression of said lower teeth therein, coating said last mentioned mold with an impressionable material, mounting said second bite plate and last mentioned mold into said registration device, inserting said second bite plate into patient's mouth to engage the upper teeth therein, closing upwardly said lower jaw and teeth for engagement with said mold and said impressionable material thereon to the extent of said second reference point as measured by said registration device, coating said second bite plate to receive therein an impression of said lower teeth forming an open-faced mold, forming a cast of mold, coating said cast with an impressionable material, mounting said second bite plate and cast upon said registration device, inserting said bite plate and cast to engage said upper denture in said patient's mouth, closing upwardly said lower teeth and lower jaw for a distance as measured by said registration device to the extent of said reference point squeezing excess impressionable material from said cast and providing a vertical position and a vertical dimension for said cast equivalent to he vertical dimension of the lower teeth, and removing said cast from said second bite plate, said cast forming a pattern for a lower denture to be made therefrom, whereby said upper and lower dentures have the same positions and provide the same occlusion as the teeth replaced.

3. A device ascertaining for denture patterns the positions in a patient's mouth of the natural teeth for replacement by dentures, comprising a dual function vertical channel member having side walls, measuring means carried by said channel member, a bite plate holding member carried by said channel member for inserting a bite plate into a patient's mouth against the upper teeth therein, said measuring means for ascertaining the distance between said bite plate and the base of the patient's nose for the vertical position of the pattern for an upper denture, a rail in said channel member, an outward angle& bracket slidably mounted on said rail, a shoulder bracket pivoted to said last mentioned bracket adapted to engage the patient's lower jaw, means carried by said channel member for elevating, said shoulder bracket, said bite plate holding member for inserting a bite plate in said patient's mouth against the upper teeth therein, and said last mentioned means for measurably elevating said shoulder bracket and with relation to said mentioned bite plate for the vertical position and vertical dimension of the pattern for the lower denture.

4. A device for denture patterns to provide the same occlusion as that of natural teeth, comprising a dual-function vertical channel member having side walls, measuring means mounted upon said channel member, a bite plate holding member carried by said channel member, said measuring means for ascertaining the distance between a bite plate held in a patient's mouth against the patient's upper teeth and the base of the patient's nose for a reference point to determine the vertical dimensions of an upper denture pattern, a second measuring means mounted upon said channel member for ascertaining the distance between a bite plate held in a patient's mouth against the upper teeth therein and the bottom of the patient's lower jaw for a second reference point to determine the vertical dimensions of a lower denture pattern.

5. The device of claim 4, wherein said first mentioned measuring means comprises a micrometer and a disc wheel carried by said micrometer adapted to be elevated to engage said base of a patient's nose.

6. The device of claim 4, wherein said second measuring means comprises an air cylinder and a shoulder bracket carried by said air cylinder adapted to be elevated to engage the patient's lower jaw and means measuring the distance of said elevation.

* * * * *

UNITED STATES PATENT AND TRADEMARK OFFICE
CERTIFICATE OF CORRECTION

PATENT NO. : 5,810,586
DATED : September 22, 1998
INVENTOR(S) : Fjelstad

It is certified that error appears in the above-identified patent and that said Letters Patent is hereby corrected as shown below:

Column 1, line 23, delete "occlusions" and insert --occlusion--.

Column 1, line 30, delete "having" and insert --have--.

Column 2, line 1, delete "on" and insert --of--.

Column 2, lines 23 and 26, delete "plain" and insert --plan--.

Column 3, line 24, after "thereon" delete --,--.

Column 4, line 23, delete "had" and insert --made--.

Column 5, line 3, delete "be continued" and insert --continue--.

Column 5, line 10, delete "has" and insert --have--.

Column 5, line 59, delete "nature" and insert --natural--.

Column 5, line 67, delete "as the" and insert --as that--.

UNITED STATES PATENT AND TRADEMARK OFFICE
CERTIFICATE OF CORRECTION

PATENT NO. : 5,810,586
DATED : September 22, 1998
INVENTOR(S) : Fjelstad

It is certified that error appears in the above-identified patent and that said Letters Patent is hereby corrected as shown below:

Column 6, line 13, after "course" insert --,--.

Column 8, line 12, delete "he" and insert --the--.

Column 8, line 35, delete "angle&" and insert --angled--.

Signed and Sealed this

Twenty-fifth Day of May, 1999

Attest:

Q. TODD DICKINSON

*Attesting Officer*     *Acting Commissioner of Patents and Trademarks*